United States Patent
Das et al.

(10) Patent No.: US 10,155,776 B2
(45) Date of Patent: Dec. 18, 2018

(54) METHOD FOR SELECTIVE DETECTION AND ESTIMATION OF HISTIDINE AND CYSTEIN

(71) Applicant: Council of Scientific and Industrial Research, New Delhi (IN)

(72) Inventors: Amitava Das, Pune (IN); Samit Chattopadhyay, Pune (IN); Upendar Reddy Gandra, Pune (IN); Hridesh Agarwalla, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 81 days.

(21) Appl. No.: 15/321,622

(22) PCT Filed: Jun. 18, 2015

(86) PCT No.: PCT/IN2015/000250
§ 371 (c)(1),
(2) Date: Dec. 22, 2016

(87) PCT Pub. No.: WO2015/198341
PCT Pub. Date: Dec. 30, 2015

(65) Prior Publication Data
US 2017/0240568 A1    Aug. 24, 2017

(30) Foreign Application Priority Data
Jun. 25, 2014   (IN) ............................ 1697/DEL/2014

(51) Int. Cl.
*C07F 1/00* (2006.01)
*G01N 33/68* (2006.01)
*G01N 33/58* (2006.01)

(52) U.S. Cl.
CPC ........... *C07F 1/005* (2013.01); *G01N 33/582* (2013.01); *G01N 33/6815* (2013.01)

(58) Field of Classification Search
CPC .... C07F 1/005; G01N 33/582; G01N 33/6815
See application file for complete search history.

(56) References Cited

U.S. PATENT DOCUMENTS 6,083,758 A * 7/2000 Imperiali ............... G01N 33/68
436/527

OTHER PUBLICATIONS

Reddy; Chemical Communication; 2014, 50, 9899.*
Du, Jao, et al., "An Highly selective fluorescent recognition of histidine by a crown ether-terpyridine-Zn (II) sensor", Chem. Commun., 49, (2013), 5399-5401.
Mitra, Atanu, et al., "Diimino conjugate of glucosyl-cresol as receptor for Cu2+ and its complex for cysteine and histidine", Trends in Carbohydrate Research , 5(4), (2013), 20-24.
Ojida, A., et al., "Molecular Recognition and Fluorescence Sensing of Monophosphorylated Peptides in Aqueous Solution by Bis(zinc(II)-dipicolylamine)-Based Artificial Receptors", J. Am. Chem. Soc., 126, (2004), 2454-2463.
International Patent Application No. PCT/IN2015/000250, Search Report and Written Opinion dated Oct. 14, 2015, 8 pgs.

* cited by examiner

*Primary Examiner* — Pancham Bakshi
(74) *Attorney, Agent, or Firm* — Schwegman Lundberg & Woessner, P.A.

(57) ABSTRACT

The Invention relates to a novel receptor molecule for estimation of amino acids based on florescence enhancements. Particularly, the invention relates to a novel Cu (II)-complex as a turn-on luminescence probe for selective detection of cysteine and histidine in pure aqueous environment and in biological sample as well as for detection of cyanide ions among various anions under physiological conditions.

15 Claims, 6 Drawing Sheets

METHOD FOR SELECTIVE DETECTION AND ESTIMATION OF HISTIDINE AND CYSTEIN

CLAIM OF PRIORITY

This application is a U.S. National Stage Filing under 35 U.S.C. 371 from International Application No. PCT/IN 2015/000250, filed on Jun. 18, 2015, and published as WO 2015/198341Al on Dec. 30, 2015, which claims the benefit of priority to India Patent Application No. 1697/DEL/2014, filed on Jun. 25, 2014, each of which is hereby incorporated by reference herein in its entirety.

FIELD OF THE INVENTION

The invention relates to a novel fluorescent probe for estimation of Cysteine and Hisidine. Particularly, the invention relates to a novel Cu(II) complex as a 'turn on' luminescence probe for selective detection of cysteine and histidine in pure aqueous environment and in biological sample as well as for detection of cyanide ions among various anions under physiological conditions.

BACKGROUND AND PRIOR ART OF THE INVENTION

Cysteine (Cys) and Histidine (His) play a crucial role in human pathologies. Among these, Cysteine acts as an intracellular redox buffer that influence detoxification and critical metabolic functions. Deficiency in Cysteine causes oxidative damage, haematopoiesis, psoriasis, leucocyte loss and metabolic disorders. Higher level of Cysteine in the human blood plasma (HBP) is known to cause cardiovascular and Alzheimer's diseases. Histidine can act as a neurotransmitter in the central nervous system of mammals. Its deficiency could affect human growth factor and may cause the impaired nutritional state of patients with chronic kidney disease. Higher level of Histidine could cause metabolic disorders like histidinemia. Estimation of these levels in blood plasma is essential for understanding the role of these groups in the pathogenesis of vascular diseases, specifically Cysteine and Histidine sensors are required.

Molecular probes are reported for vital biothiols, like cysteine (Cys) and histidine (His), however, examples of molecular probes capable of detecting Cysteine and Histidine in biological fluids in presence of homocysteine (Hcy) and glutathione (GSH) are rather limited. Molecular probes that are generally being used for detection of biothiols either in physiological condition or in biological fluids are mostly based on chemodosimetric reaction and such process often suffers from the relatively large incubation time ranging from 20 minutes to 1 hr or more. Alternate approach utilizes the higher affinity of Cu(II) towards S-donor nucleophiles for designing molecular probes with fluorescence on response. Such reactions mostly happen within millisecond time scale and thus, this methodology has an edge over the other. Among various molecular probes that are specific towards Cysteine without any interference from Hcy and GSH and work in pure physiological conditions are rather rare, while such limited probes are known for Histidine. However, majority of such reagents relied on chemodosimetric detection and estimation of the total thiol content in human blood plasma (HBP). Use of certain fraction of organic solvents was described in most such reports for solubilising the reagent.

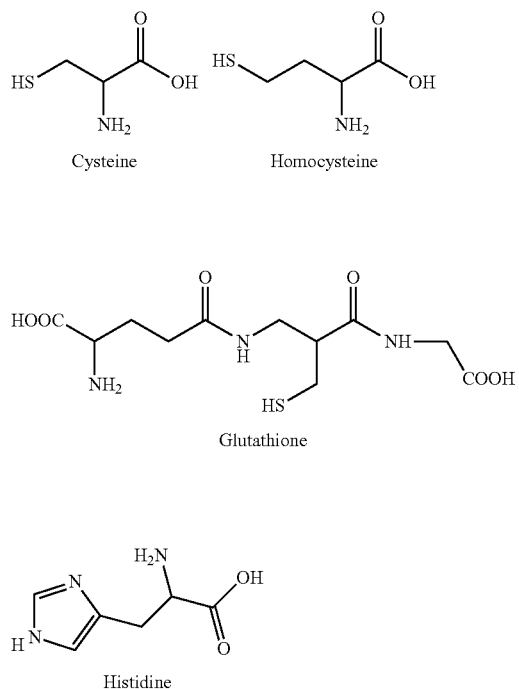

Cysteine

Homocysteine

Glutathione

Histidine

Article titled 'An Highly selective fluorescent recognition of histidine by a crown ether-terpyridine-Zn (II) sensor' by Jiao Du et. al published in Chem. Commun., 2013, 49, 5399-5401 disclose a Zn (II) complex that exhibits enhanced fluorescence in the presence of histidine but not in the presence of any other amino acids including cysteine. This sensor could also distinguish histidine from other imidazole derivatives.

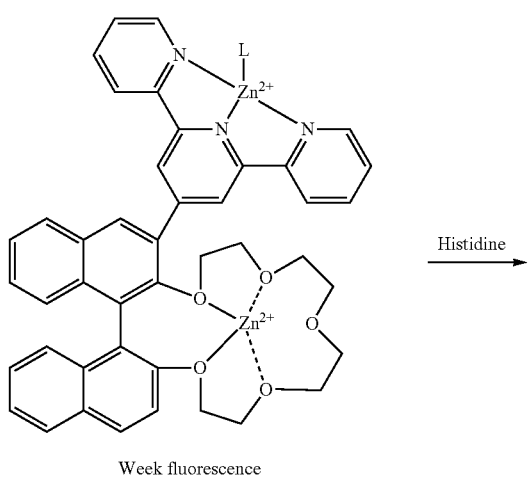

Week fluorescence

-continued

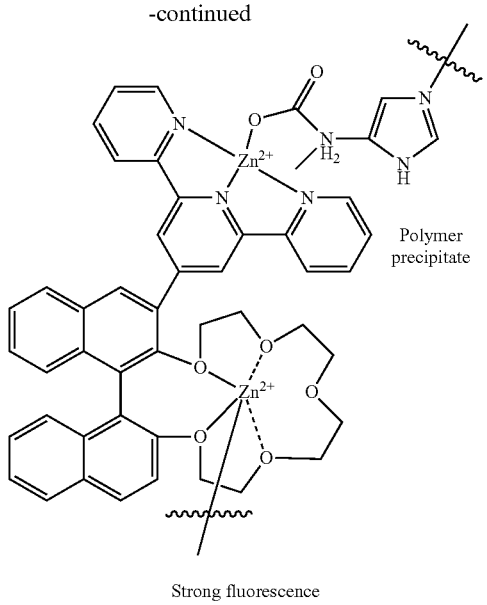

Strong fluorescence

Article titled "Diimino conjugate of glucosyl-cresol as receptor for $Cu^{2+}$ and its complex for cysteine and histidine' by Atanu Mitra et. al. in trends in carbohydrate research, vol 5, no. 4(2013) 20-24 disclose a calorimetric approach for $Cu^{2+}$ sensing on a Diimino conjugate of glucosyl cresol (L). The chemo sensor (L) with $Cu^{2+}$ is used for detecting cysteine and histidine by absorption and calorimetric titrations. Further, synthesis of chemo sensor (L) comprises single one step condensation of glucosamine with 2,6-dioxo-4-methyl-1-hydroxy benzene (2) as shown in scheme below:

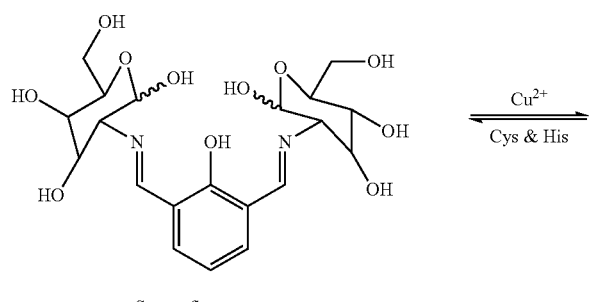

Strong fluorescence

Complexation of metal ion with dipicolylamine (DPA) ligand as chemical sensors for peptides, amino acids is explored in the art. An article titled 'Molecular Recognition and Fluorescence Sensing of Monophosphorylated Peptides in Aqueous Solution by Bis(zinc(II)-dipicolylamine)-Based Artificial Receptors' by Akio Ojida et al. J. Am. Chem. Soc., 2004, 126 (8), pp 2454-2463 fluorescent chemosensors bearing two zinc ions coordinated to distinct dipicolylamine (Dpa) sites. Fluorescence titration experiments show the selective and strong binding toward phosphate derivatives in aqueous solution. The chemosensors showed clear distinction between phosphorylated and nonphosphorylated peptides and strong binding to a negatively charged phosphorylated peptide.

Prior art search reveals that there remains a need in the art for quick and reliable approach for detection of Histidine and Cysteine in aqueous medium or physiological fluids, without the interference of other amino acids or specifically, glutathione.

The promising role of metal ion complex with dipcolylamine crafted on fluorophores which can show 'turn on' type fluorescence enhancement encouraged the present inventors to provide novel receptor molecule using novel ligand for selective and instantaneous detection of cysteine and histidine among the ensemble of amino acids under physiological conditions.

OBJECTIVE OF THE INVENTION

The main objective of the present invention is to provide novel fluorescent probe for estimation of Cysteine and Histidine. Another objective of the invention is to provide a method of quantitative estimation of Histidine and Cysteine using novel Cu(II) complex (R) in a biological sample.

One more objective of the invention is to provide a kit for the estimation of Histidine and Cysteine in a biological sample.

SUMMARY OF THE INVENTION

Accordingly, the present invention provides a novel fluorescent probe for estimation of Cysteine and Histidine. Another object of the present invention provides a novel bis-Cu(II)-complex (R) of receptor ligand bis-dipicolyl amine derivative (L) as fluorescence probe for selective detection of cysteine and histidine in pure aqueous environment and in a biological sample as well for specific imaging of endogenous Cysteine in live Hct116 cells without any interference from other amino acids;

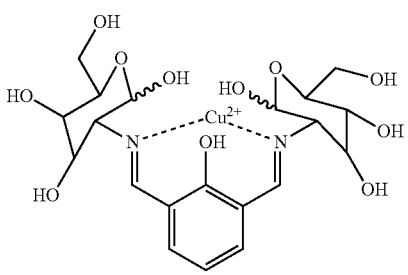

Weak fluorescence

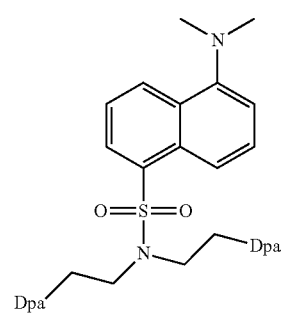

L

-continued

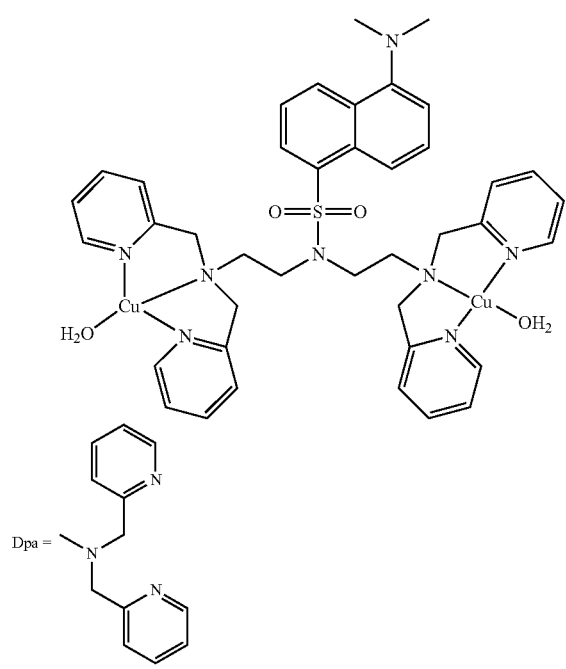

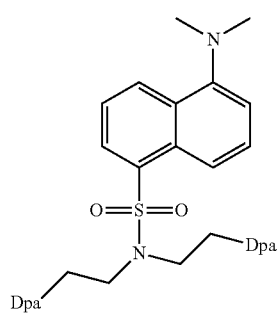

In another embodiment, the present invention provides novel ligand bis-dipicolyl amine derivative (L) that can coordinate with a metal ion for fluorescent sensing

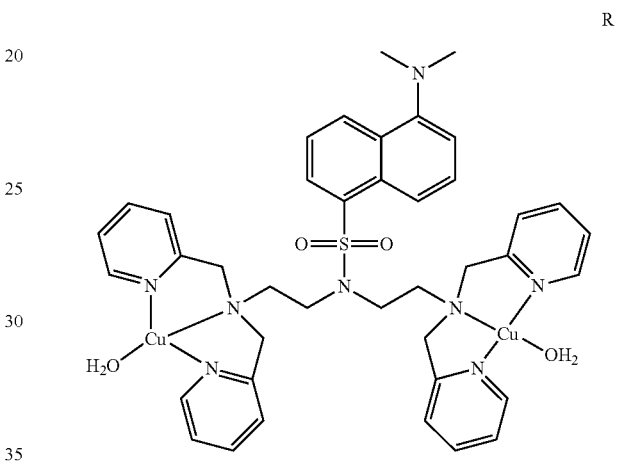

In another embodiment, the present invention provides a process for synthesis of bis-Cu(II)-complex (R) of receptor ligand bis-dipicolyl amine derivative (L).

In another embodiment, the present invention provides a method for quantitative estimation of cysteine and histidine in a biological sample without any interference from other amino acid by reacting the bis-Cu(II)-complex (R) of ligand bis-dipicolyl amine derivative (L) with a biological sample in pure aq.-HEPES buffer medium (pH 7.4).

In yet another embodiment, the present invention provides a method for specific imaging of endogenous Cysteine in live Hct116 cells without any interference from other amino acid by reacting the bis-Cu(II)-complex (R) of ligand bis-dipicolyl amine derivative (L) with live cells in pure aq.-HEPES buffer medium (pH 7.4).

In another embodiment, Luminescence spectra of the Ligand R in the absence and presence of 100 mole equivalent of various anionic analytes like $F^-$, $Cl^-$, $Br^-$, $I^-$, $CN^-$, $CH_3CO_2^-$, $H_2PO_4^-$, $P_2O_7^{4-}$, $HSO_4^-$, $NO_3^-$, $NO_2^-$, $N_3^-$, $ClO_4^-$, $PhCO_2^-$ and $IO_4^-$ in buffer media (pH 7.4) was recorded. Among all these anions, only $CN^-$ showed a turn-on emission response with maximum at 552 nm. Thus, along with Histidine and Cysteine, this reagent could also be used for detection of cyanide under the physiological condition.

In yet another embodiment, the invention provides a kit comprising the bis-Cu (II)-complex (R) of ligand bis-dipicolyl amine derivative (L) for quantitative estimation of Histidine and Cysteiene as well as for specific imaging of endogenous Cysteine in live Hct116 cells in aqueous medium or physiological fluids.

In another embodiment, the invention provides imaging of Cysteine intracellularly.

In an embodiment of the invention it provides a compound of formula R

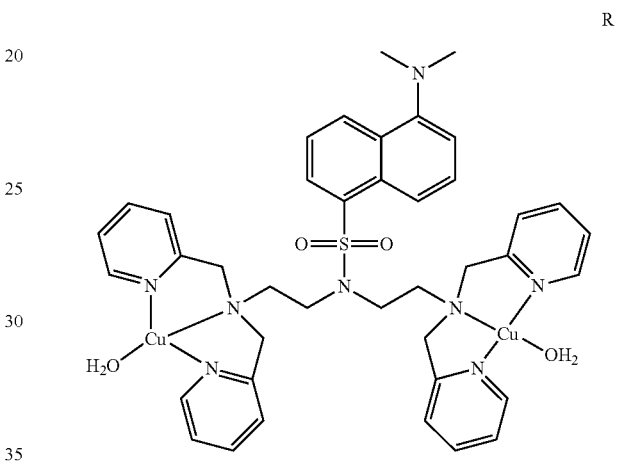

In an embodiment of the invention it provides a compound useful as a fluorescent probe for selective detection and estimation of amino acids.

In an embodiment of the invention it provides a compound wherein the amino acids are selected from the group consisting of cysteine and histidine.

In an embodiment of the invention it provides a process for synthesis of the compound comprising the process steps as:
a. heating the solution of mixture of 5-amino-N,N-bis(2-aminoethyl) naphthalene-1-sulfonamide,2-pyridine carboxaldehyde for 1 hr under heating at (65±15)° C. After 1±0.5 hr allowed the reaction mixture to room temperature add the reducing agent stir the reaction mixture for (48±4) hr to obtain ligand (L);

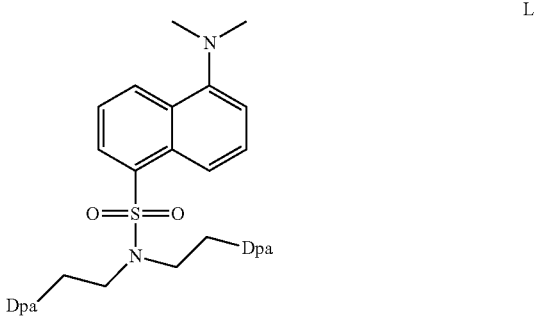

b. reacting ligand (L) obtain in step (a) with catalyst (add more if workable because its restrict the claim) at temperature ranging between (65±15)° C. to room temperature in a solvent to obtain Cu (II) complex (R).

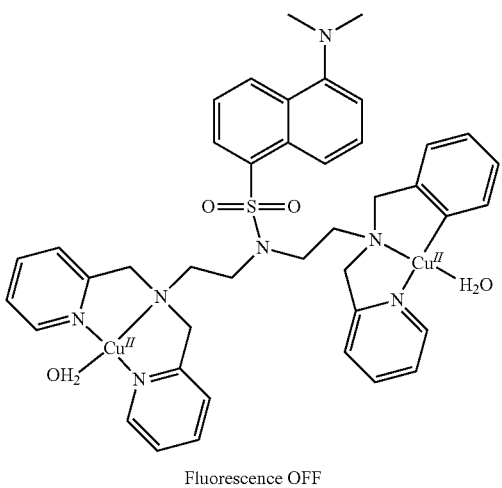

Fluorescence OFF

In an embodiment of the invention the solvent is 1,2-dichloro methane.

In an embodiment of the invention the reducing agent is Sodium triacetoxyborohydride.

In an embodiment of the invention the reducing agent is Sodium bhorohydride.

In an embodiment of the invention it provides a method for detection of total cysteine and histidine present in a biological sample using the compound comprising;
  i. providing a biological sample consisting an ensemble of all natural amino acids;
  ii. adding N-Ethylmaleimide (NEM) to the biological sample obtained in step (i);
  iii. spiking the biological sample pre-treated with NEM obtained in step (ii) with known amount of histidine;
  iv. adding bis-Cu (II) complex reagent (R) to the above solution of step (iii);
  v. providing control comprising pure aqueous HEPES buffer solution having pH of 7.4 of histidine;
  vi. illuminating the sample solution and pure aqueous HEPES buffer solution having pH of 7.4 of histidine;
  vii. quantifying the amount of histidine and cysteine present in the sample solution.

In an embodiment of the invention the concentration of HBP is in the range of 15-25 µM.

In an embodiment of the invention the concentration of NEM is in the range 7.5-12 mM.

In an embodiment of the invention the concentration of bis-Cu (II) complex reagent (R) is in the range 15-25 µM.

In an embodiment of the invention it provides a method for detecting intracellular cysteine comprising;
  i. incubating live Hct116 cells with bis-Cu (II) complex reagent (R) in aq.-HEPES buffer solution or optionally pre-treating the cells with NEM;
  ii. washing the solution obtained in step (i) with phosphate buffer solution (PBS);
  iii. providing a control comprising of live Hct116 cells without bis-Cu (II) complex reagent (R) in aq.-HEPES buffer solution;
  iv. illuminating the above solution and determining the bright-red fluorescent image of reaction of R with intracellular Cysteine.

In an embodiment of the invention it provides a method for detecting cyanide ions among various anionic analytes under physiological conditions comprising reacting the solution containing various anions in aq.-HEPES buffer pH 7.4 with bis-Cu (II)-complex (R) of claim 1 and illuminating the sample and detecting the luminescence spectra.

In an embodiment of the invention it provides a kit for carrying out the method for selective detection of cysteine and histidine without any interference from other amino acids according to any of the preceding claims comprising;
  i. bis-Cu (II)-complex (R) of receptor ligand bis-dipicolyl amine derivative (L) of concentration 10 µm as fluorescent probe, excitable by spectrally separated wavelength of light, in pure aq.-HEPES buffer (pH 7.4) medium;
  ii. 1 mM NEM solution;
  iii. standard solution of histidine of concentration of 200 µM and 300 µM in pure aq.-HEPES buffer (pH 7.4) medium; and
  iv. Instruction manual for performing the method.

In an embodiment of the invention a kit for carrying out the method for detection of cyanide ions among various anions under physiological conditions according to any of the preceding claims comprising;
  i. bis-Cu (II)-complex (R) of receptor ligand bis-dipicolyl amine derivative (L) of concentration 10 µm as fluorescence probe, excitable by spectrally separated wavelength of light, in pure aq.-HEPES buffer (pH 7.4) medium;
  ii. one or more standard solution in pure aq.-HEPES buffer (pH 7.4) medium; and
  iii. Instruction manual for performing the method.

In an embodiment of the invention it provides use of bis-Cu (II)-complex (R) of receptor ligand bis-dipicolyl amine derivative (L) as fluorescence probe for detection of cyanide ions among various anions under physiological conditions.

DETAILED DESCRIPTION OF THE INVENTION

The invention will now be described in detail in connection with certain preferred and optional embodiments, so that various aspects thereof may be more fully understood and appreciated.

Accordingly, to achieve the objectives of the invention, novel bis-dipicolyl amine derivative (L) and its corresponding binuclear Cu (II)-complex (R) are disclosed for instantaneous and selective detection of cysteine and histidine in HBP as well as endogenous cysteine.

Among the biothiols cysteine has lower pKa value of the thiol group in the side chain (8.00), as compared to that in homocysteine (Hcy; 8.87) and glutathione (GSH, 9.20). This factor is used in the present invention for the specific detection of cysteine without any interference from these two commonly interfering biothiols at pH 7.4. At pH 7.4, cysteine exists predominantly in its thiolate form and thus acts as a better coordinating ligand for Cu (II) than other biothiols. Further, histidine is known to form a stable complex with Cu (II) and is utilized in the present study for its recognition.

Thus, in a preferred embodiment, the present invention discloses novel bis-Cu (II)-complex (R) of ligand bis-dipicolyl amine derivative (L) as 'turn on' fluorescence probe for selective detection of cysteine and histidine in pure aqueous environment and in a biological sample as well for specific imaging of endogenous Cysteine in live Hct116 cells without any interference from other amino acids;

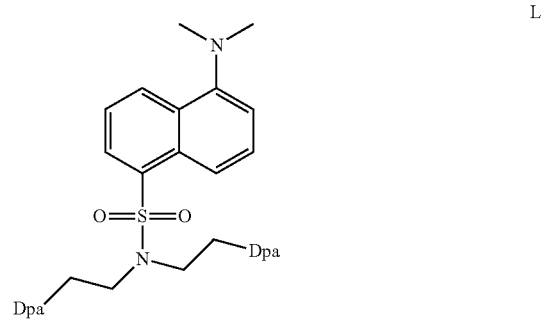

The present invention discloses novel bis-Cu (II)-complex (R) of ligand bis-dipicolyl amine derivative (L) as 'turn on' fluorescence probe for detection of cyanide ions among other various anions under physiological conditions.

Figure 1:
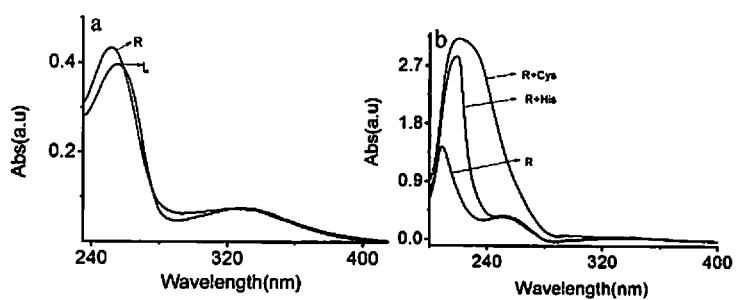
FIG. 1 depicts (a) Absorbance spectra of L ($2.0\times10^{-5}$ M) and R ($2\times10^{-5}$ M) (b) Absorbance spectra of R ($2.0\times10^{-5}$ M) in presence of His and Cys were performed in 10 mM HEPES buffer (pH 7.4) medium.
Figure 2:
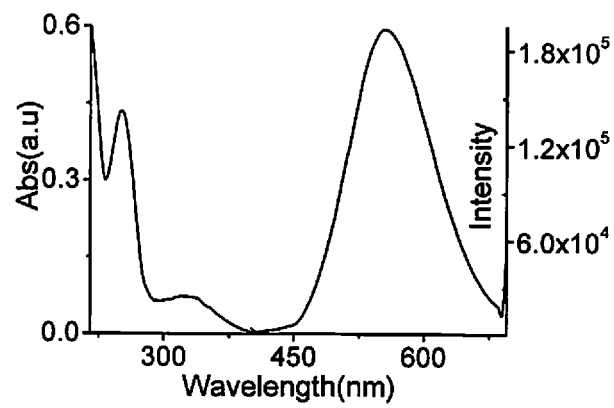
FIG. 2 depicts Electronic and luminescence ($\lambda_{Ext}$=350 nm) spectra of L ($2\times10^{-5}$ M) in aq. HEPES buffer acetonitrile (96:4 (v/v); pH 7.4).

The present invention relates to novel ligand bis-dipicolyl amine derivative (L) that can coordinate with a metal ion for fluorescent sensing;

In an aspect, the purity of ligand (L) and the reagent (R) was determined by analytical and spectroscopic studies. The studies with ligand (L) were performed in the aqueous HEPES buffer-acetonitrile (96:4 (v/v); pH 7.4) medium, while studies with reagent (R) were performed in pure aq.-HEPES buffer (pH 7.4) medium. The said novel receptor (L) and the reagent (R) were characterized by mass spectroscopy, Uv-vis spectroscopy as depicted in FIGS. 1-2.

Accordingly, Uv-vis spectrum of ligand (L) showed two distinct bands at 256 nm and 329 nm and two bands for reagent (R) appeared at 252 and 324 nm, respectively. The band at 256 nm for (L) was attributed to a charge transfer (CT) transition involving $N_{Amine}$ as a donor and a dansyl moiety (5-naphthalene-1-sulfonyl chloride) as an acceptor. The other band at 329 nm was ascribed to a dansyl-based CT transition. Observed blue shifts in (R) were ascribed to a less favored CT process, as compared to those in (L).

Reagent R is a Cu (II)-complex. Being a $d^9$ (paramagnetic) system, no sensible NMR spectra is obtained either in absence or in presence of His and Cys. Whereas L without Cu (II)-centere doesn't not bind to Cys or His.

The Novel bis-Cu (II)-complex (R) and ligand (L) are characterized by emission spectra under excitation at 350 nm.

Figure 3A:
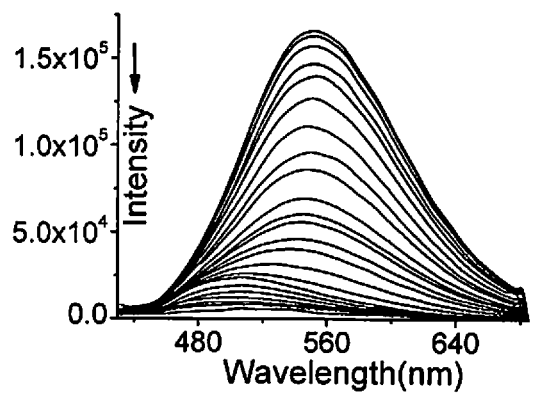
FIG. 3 depicts Emission spectral responses of L ($2.0\times10^{-5}$ M) towards varying [Cu(ClO$_4$)$_2$](0 to $4.6\times10^{-5}$ M) in aq.-HEPES buffer-CH$_3$CN (96:4 (v/v); pH 7.4) medium using $\lambda_{Ext}$=350 nm and Slit width 3 nm. Inset titration profile. 7 (a) B-H plot of L ($2\times10^{-5}$M) for varying [Cu$^{2+}$] (0 to $4.6\times10^{-5}$ M) λext=350 and $\lambda_{Mon}$=552 nm. Good linear fit confirms the 1:2 binding stoichiometry in aq.-HEPES buffer-CH$_3$CN (96:4(v/v); 10 mM, pH 7.4) medium. (b) Luminescence titration profile.

X-band EPR spectrum of probe R (1.0 mM) in the absence and presence of Cys (3.0 mM) and His (3.0 mM) were recorded. All studies were performed in aq.-HEPES buffer (10 mM, pH 7.4) medium at 298±20 K Further, Fluorescence responses of L ($2.0\times10^{-5}$ M) towards varying concentration of $Cu^{2+}$ [$Cu(ClO_4)_2$; at 0 to $4.6\times10^{-5}$M) was performed in aq.-HEPES (4-(2-hydroxyethyl)piperazine-1-ethanesulfonic acid) buffer-$CH_3CN$ (96:4 (v/v); pH 7.4) medium at room temperature (FIG. 3). A strong emission band at $\lambda_{max}$ of 552 nm ($\Phi$=0.068 for $\lambda_{Ext}$ of 350 nm and dansyl amide as a standard) was observed. Hypsochromic shift ($\Box\lambda_F$) of 52 nm in emission maxima was observed upon binding of L to $Cu^{2+}$ with quenching of the dansyl-based fluorescence. Binding of the $Cu^{2+}$ ($d^9$-system) was accounted for the observed luminescence quenching. The new but weak CT-based emission band with maxima at ~500 nm confirmed formation of a bis-Cu (II) complex with ligand (L).

Figure 3B:
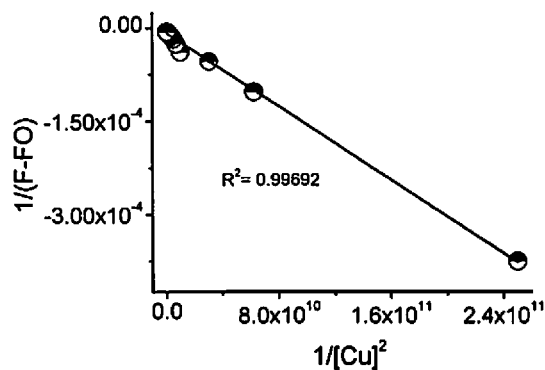

The B-H (Benesi-Hildebrand) plot revealed al: 2 binding stoichiometry and a binding constant of $(4.2\pm0.02)\times10^8 M^{-2}$ for formation of R upon interaction of L with $Cu^{2+}$ (FIG. 3*b*).

Figure 4:
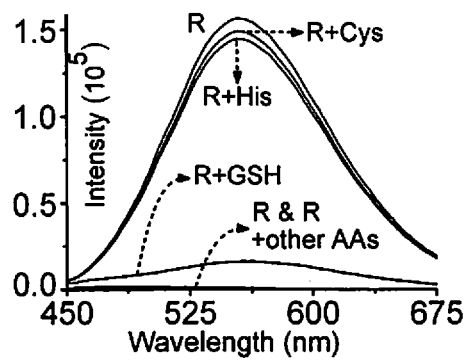
FIG. 4 depicts Luminescence spectra of R ($2.0\times10^{-5}$ M) in the absence and presence of various amino acids (AAs); e.g. tryptophan (Trp), leucine (Leu), isoleucine (Ile), methionine (Met), threonine (Thr), tyrosine (Tyr), valine (Val), alanine (Ala), serine (Ser), glycine (Gly), cysteine (Cys), Glutathione (GSH), homocysteine (Hey), proline (Pro) and arginine (Arg) in pure aq.-HEPES buffer medium.
Figure 7:
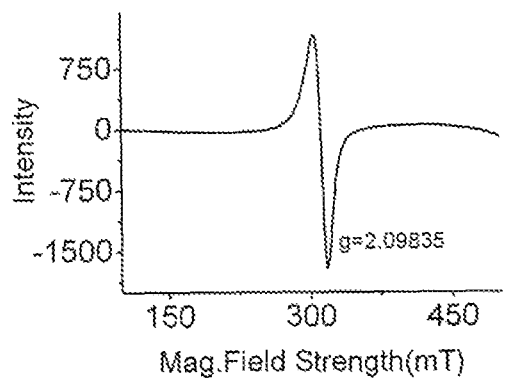
FIG. 7 depicts X-Band EPR spectrum of complex R recorded in aqueous medium at room temperature.
Figure 8:
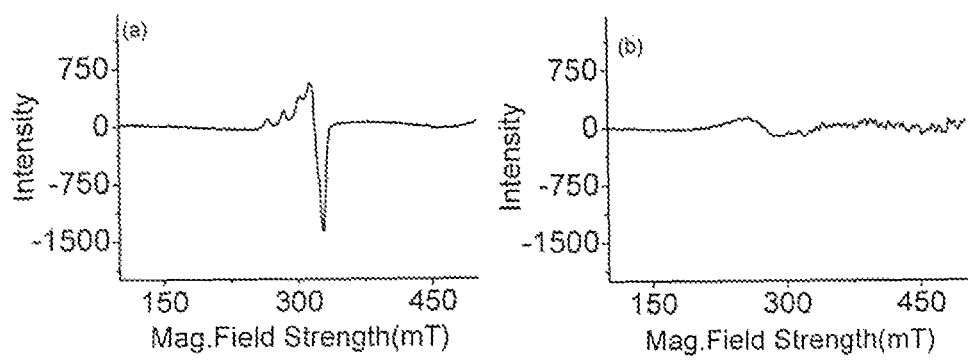
FIG. 8 depicts (a) X-Band EPR spectrum of complex R in presence of His (b) R in presence of Cys recorded in aqueous medium at room temperature.
Figure 9:
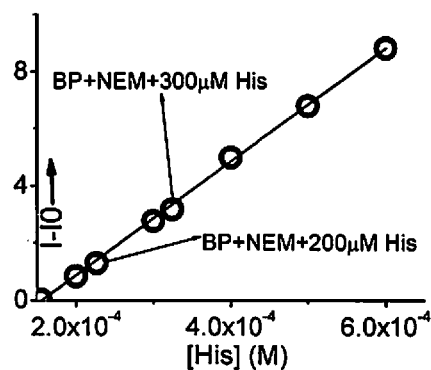
FIG. 9 depicts Plot of $\Delta I=(I_0-I)$ vs. [His], where $I_0$ and I are emission intensities of receptor R at 552 nm ($I_{Ext}=350$ nm) inpresence of known [His] and blood plasma samples spiked with a known [His]+10 mM NEM.
Figure 10:
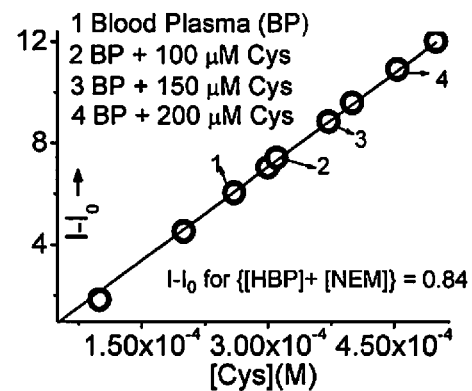
FIG. 10 depicts Plot of $\Delta I=(I_0-I)$ vs. [Cys], where $I_0$ and I are emission intensities of receptor R at 552 nm ($I_{Ext}=350$ nm) in the absence and presence of known [Cys] and blood plasma/blood plasma samples spiked with a known [Cys].

The Luminescence spectra for R ($2.0\times10^{-5}$ M) ($\lambda_{Ext}$=350 nm) in the absence and presence of 200 mole equivalent of various amino acids were recorded in pure aq.-HEPES buffer medium (pH 7.4) and are shown in FIG. 4. The studies revealed that increase in emission intensity was observed at 552 nm when Cysteine or Histidine was added to the aq.-buffer solution of R. Unlike Cysteine/Histidine, other thio-amino acids such as Hey and GSH could not induce such emission enhancement. Electron Spin resonance spectroscopy (ESR) spectra of R in absence and presence of Cysteine and Histidine in pure aq.-HIEPES buffer media (pH 7.4) are shown as an inset in FIGS. 7&8.

The emission spectra of R ($2.0\times10^{-5}$ M) in presence of Histidine and Cysteine were recorded under excitation at 350 am in 10 mM HEPES buffer pH (7.4) medium.

The present invention discloses a process for the synthesis of L and R comprising the steps of:
a. heating solution mixture of compound (1), 2-pyridine carboxaldehyde and sodium triacetoxyborohydride for several hours until completion of reaction to obtain ligand (L); and
b. reacting ligand (L) with $Cu(ClO_4)_2.6H_2O$ at $(25\pm3)^\circ$ C. in a solvent to obtain Cu(II) complex (R).

The process is depicted in Scheme 1 below:

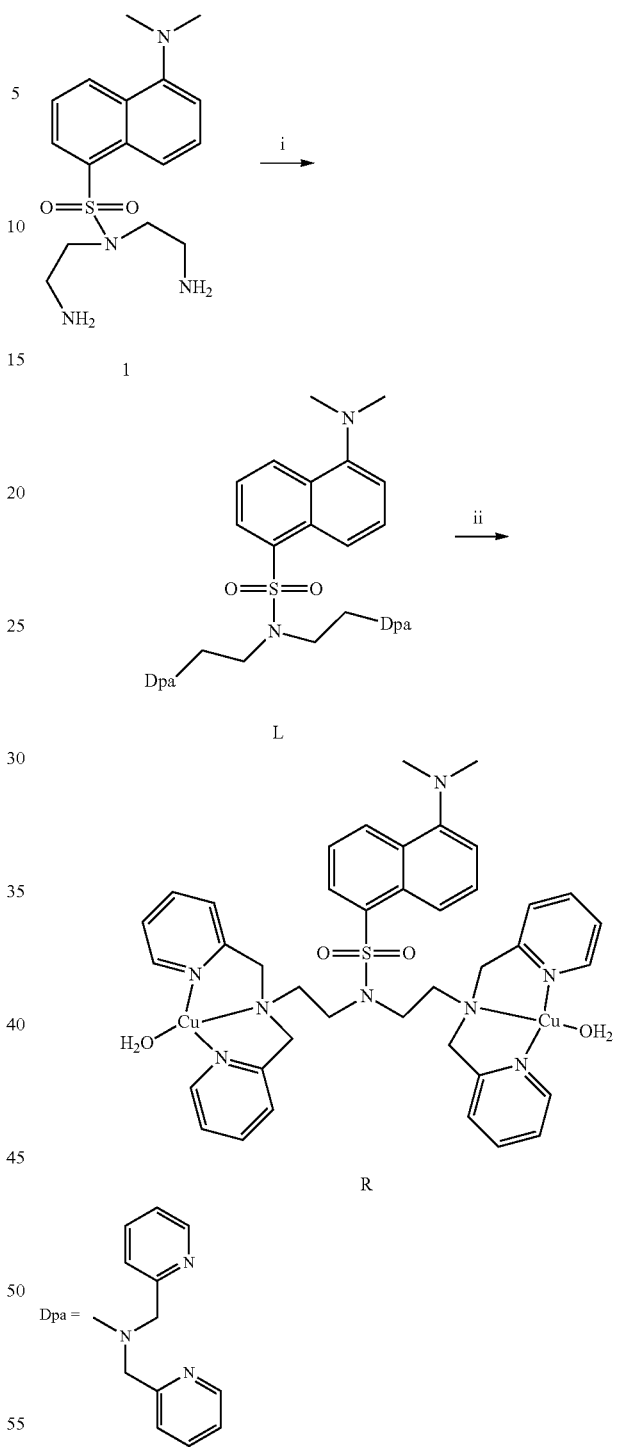

i. 2-Pyridine carboxyldehyde, NaBH(OAC)$_3$, 1,2 Di chloroethane, RT, 48 h.
ii. Cu(ClO$_4$)$_2$.H$_2$O, MeOH, RT, 8 h.

The compound (1) was obtained by refluxing solution of diethylene triamine with phthalic anhydride to obtain compound (a); reacting compound (a) with dansyl chloride (5-naphthalene-1-sulfonyl chloride) in presence of base and solvent to obtain compound (b) followed by hydrolysis with hydrazine monohydrate to yield the desired compound (1).

The process is shown below in Scheme 2.

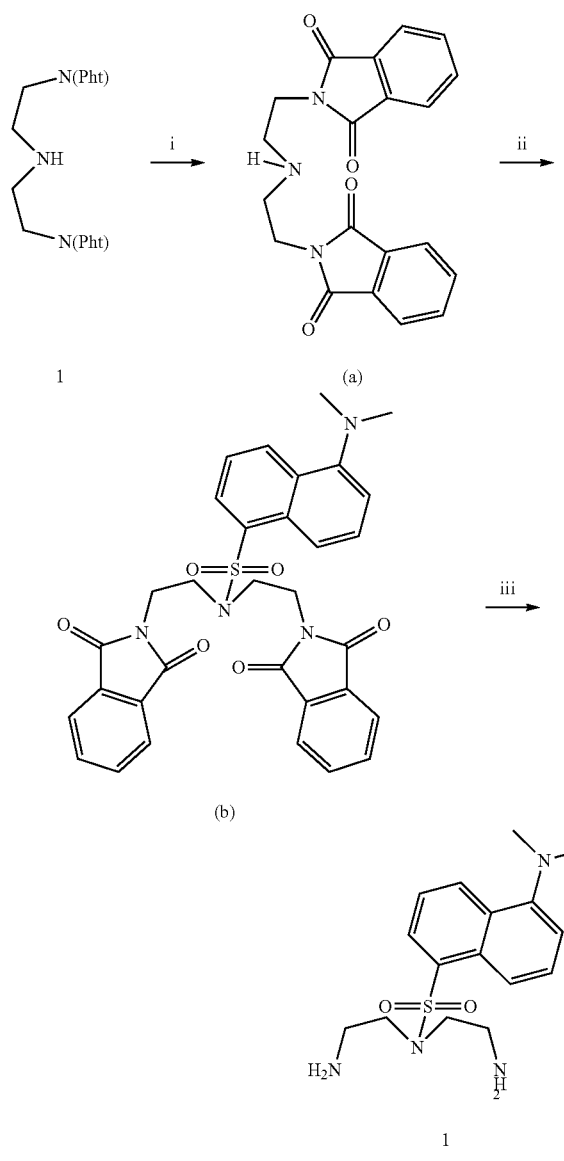

Figure 5:
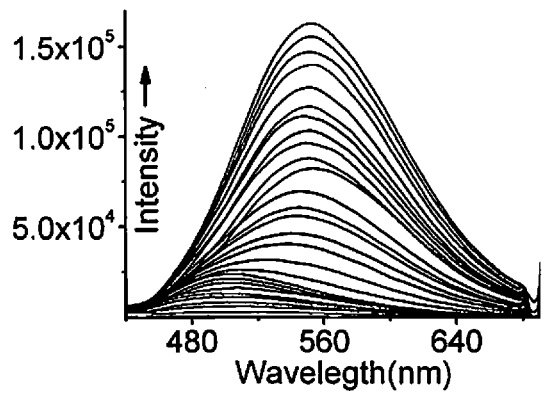
FIG. 5 depicts Changes in luminescence spectra for R ($2.0 \times 10^{-5}$ M) in presence of varying [Cys] (0 to $2.8 \times 10^{-3}$ M). Studies were performed in aq.-HEPES buffer (10 mM, pH 7.4) medium using $\lambda_{Ext}=350$ nm and Slit width 3 nm.
Figure 6:
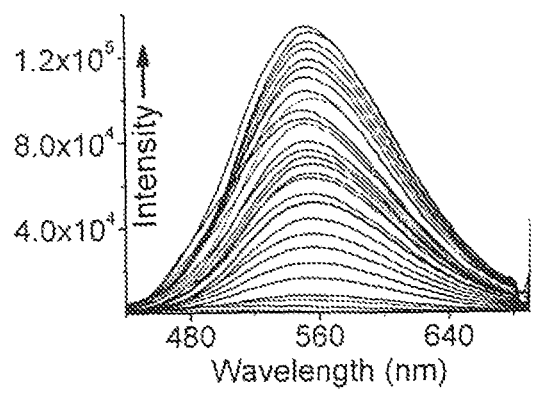
FIG. 6 depicts Changes in luminescence spectra for R ($2.0 \times 10^{-5}$ M) in presence of varying [His] (0 to $3.1 \times 10^{-3}$ M); Studies were performed in aq.-HEPES buffer (10 mM, pH 7.4) medium using $\lambda_{Ext}=350$ nm and Slit width 3 nm.

Systematic luminescence titrations were carried out for R ($2.0\times10^{-5}$ M) with varying [Cysteine] (0 to $2.8\times10^{-3}$ M) and [Histidine] (0 to $3.2\times10^{-3}$ M) concentrations in pure aq.-HEPES buffer medium (10 mM, pH 7.4). Increase in [Cysteine] or [Histidine] caused a concomitant increase in emission intensity at ~552 nm (FIGS. 5 and 6). The two independent titrations revealed linear range of 90-2800 μM and 200-3200 μM, for Cysteine and Histidine, respectively.

The increase in emission intensity as observed in systematic luminescence titrations encouraged the present inventors to use the reagent (R) for quantitative estimation of total [Cysteine] and [Histidine] present in a solution.

The present invention discloses a method for quantitative estimation of total [Cysteine] and [Histidine] present in a biological sample comprising;
i. providing biological sample consisting an ensemble of all natural amino acids;
ii. adding N-Ethylmaleimide (NEM) to the biological sample;
iii. spiking the biological sample pre-treated with NEM with known amount of histidine;
iv. adding the bis-Cu(II) complex reagent (R) to the above solution of step (iii);
v. illuminating the sample solution and pure aqueous HEPES buffer solution having pH of 7.4 of histidine;
vi. quantifying the amount of histidine and cysteine present in the sample solution.

Alternately, the amount of cysteine and histidine present in biological sample was estimated by the method which comprises;
i. providing biological sample consisting an ensemble of all natural amino acids;
ii. reacting the above biological sample with bis-Cu (II) complex reagent (R) and subjecting the solution to illumination and recording the emission spectra;
iii. treating the above solution with NEM and recording the emission spectra; and
iv. quantifying the amount of histidine and cysteine present in the sample solution.

In an aspect, the biological sample according to the preceding aspects is human blood sample (HBP).

Accordingly, the quantitative estimation of histidine in the solution mixture was performed in presence of N-Ethylmaleimide (NEM).

NEM is known to react irreversibly with Cysteine and yield a non-fluorescent compound (Scheme 3 shown below). Then this resultant solution was used for quantitative analysis of Histidine.

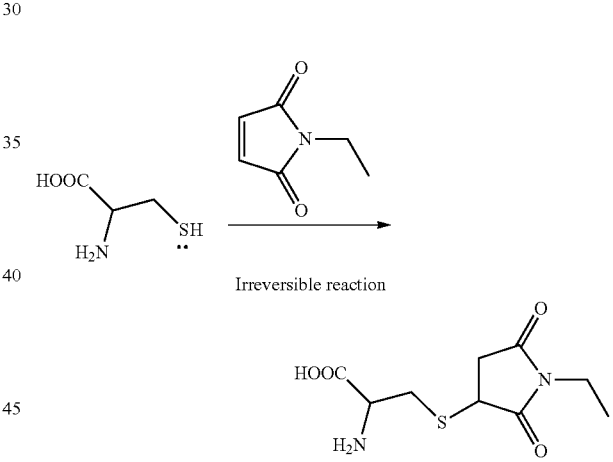

Irreversible reaction

Literature studies reveal that the respective concentration levels of Cysteine and Histidine in human blood plasma are typically 240-360 μM and 15-75 μM. Since, the concentration of Histidine in HBP is low and to avoid any error in its detection, HBP samples (pre-treated with excess NEM) were spiked with two known concentration of Histidine (200 μM and 300 μM, respectively. Emission intensities ($I_{HBP+200}$ and $I_{HBP+300}$, respectively) were recorded for these two solutions.

Average of the difference ($I_{HBP+200}-I_{200}$) and ($I_{HBP+300}-I_{300}$) led to evaluation of actual [Histidine] in HBP sample and was found to be (23±2.1) LM ($C_{His}$). Then the difference $CT-C_{His}$ yielded the actual [Cys] (239±7.5) μM in HBP sample. The evaluated [Cys] and [His] in HBP were observed within the allowed limit for a healthy human being.

In the alternate method, $C_{Cys}$ was evaluated from the experiments with NEM, which reacted specifically with Cysteine. Emission intensity for HPB samples treated with bis-Cu (II) complex reagent (R) was evaluated ($I_T$), which reflects the total concentration of Cysteine and Histidine present in HBP sample. Then this solution was treated with NEM. NEM reacted with Cysteine present in HBP sample and the product was non emissive. The emission intensity ($I_{NEM}$) for the resulting solution was evaluated and the difference in intensities ($\Box I = I_T - I_{NEM}$) was used for evaluation of [Cysteine] in HBP sample.

The source of illumination is Xenon lamp. In fluorescence studies excitation source is 350 nm for compound R and L. The concentration of HBP used in the above process is in the range of 15-25 μM; NEM in the concentration range of 7.5-12 mM and bis-Cu(II) complex reagent (R) in the concentration range of 15-25 μM.

The results are presented in FIG. 4 and the results confirmed that the reagent R can be used for selective detection for Cysteine and/or Histidine in ensemble of all other natural amino acids in pure aq. buffer medium.

The above process for the reaction of ligands L and R with Cysteine and Histidine is shown below in Scheme 2:

Scheme: 2

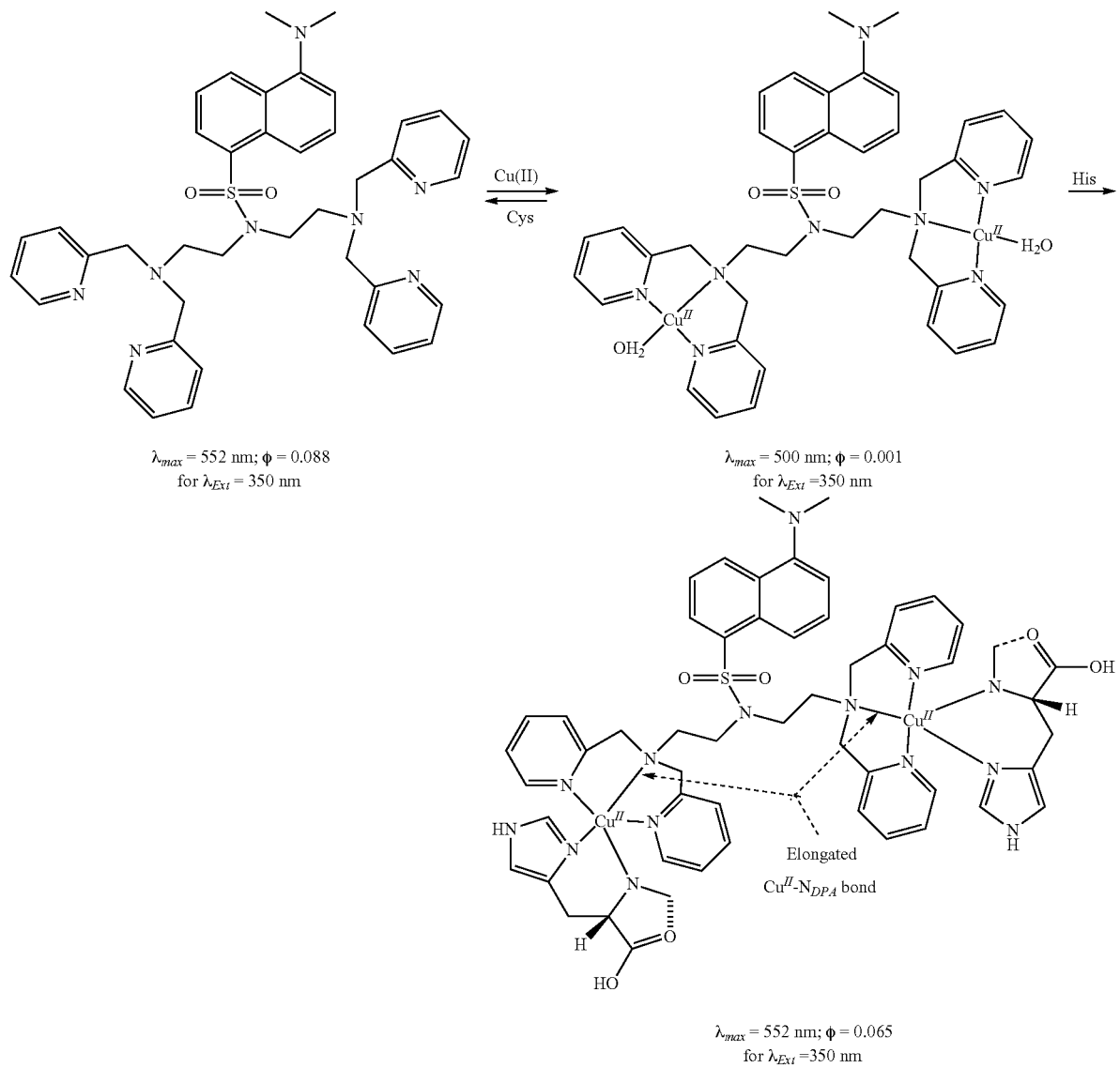

Figure 11:
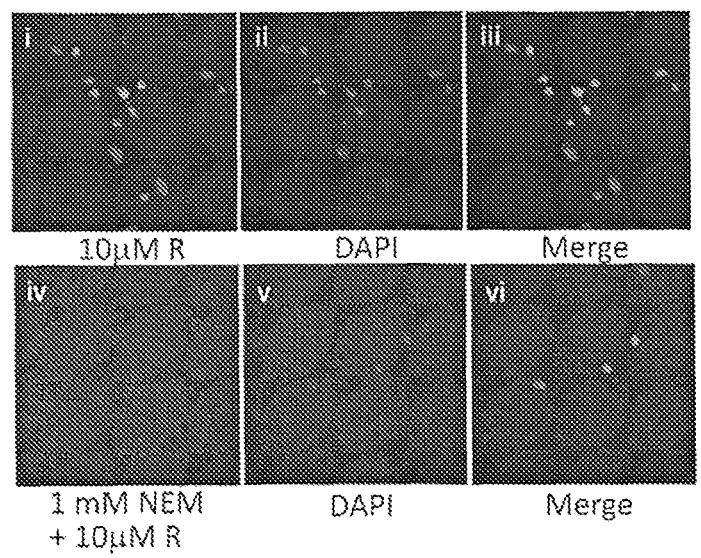
FIG. 11 depicts confocal laser fluorescence microscopic images of Hct116 cells treated with 10 μM of R in HEPES buffer; (ii, v). DAPI is added for nucleus staining agent; (iv). The cells were pre-incubated 1 mM of N-ethylmaleimide (NEM); (iii, vi). Overlay of the merged images.
Figure 12:
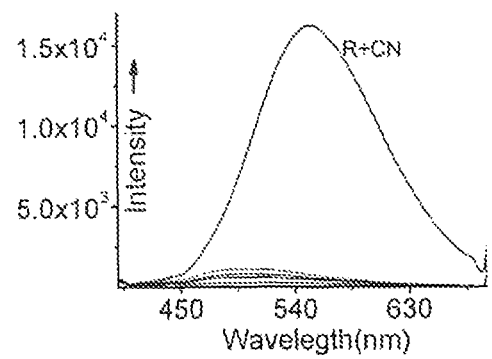
FIG. 12 depicts Luminescence spectra ($\lambda_{Ext}=350$ nm) of R in absence and presence of various anions ($X^-=F^-$, $Cl^-$, $Br^-$, $I^-$, $CN^-$, $CH_3CO_2^-$, $H_2PO_4^-$, $P_2O_7^{4-}$, $HSO_4^-$, $NO_3^-$, $NO_2^-$, $N_3^-$, $ClO_4^-$, $PhCO_2^-$ and $IO_4^-$) were performed in aq.-HEPES buffer pH 7.4.
Figure 13:
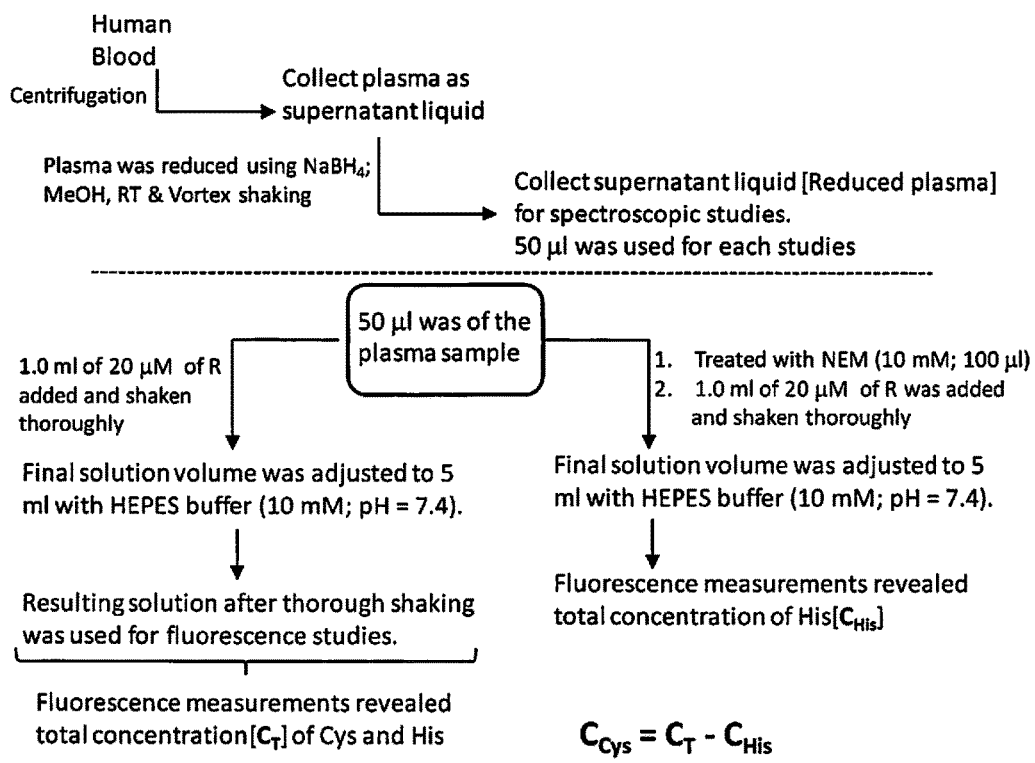
FIG. 13 depicts a schematic depicting the estimation of Histidine and Cysteine. The diagram shows the estimation from human blood.

The present invention relates to flourimetric analysis and detection of intracellular cysteine present in live Hct116 cells comprising;

i. incubating live Hct116 cells with bis-Cu(II) complex reagent (R) in aq.-HEPES buffer solution or optionally pre-treating the cells with NEM;

ii. washing the solution with phosphate buffer solution (PBS);

iii. providing a control comprising of live Hct116 cells or without bis-Cu(II) complex reagent (R) in aq.-HEPES buffer solution;

iv. illuminating the above solution and determining the bright-red fluorescent image of reaction of R with intracellular Cysteine, Accordingly, the flourimetric analysis employing R as ligand for detection of intracellular Cysteine that could be present in live Hct116 cell was studied by confocal laser microscopy. Live Hct116 cells were incubated with reagent R (10 µM) in aq.-HEPES buffer solution (pH 7.4) at 37° C. and washed repeatedly with phosphate buffer solution (PBS) to remove the surface adhered probe molecules. Control experiments were performed without exposing live Hct116 cells to the probe reagent solution; otherwise maintaining the identical experimental conditions. The bright-red fluorescence images were observed from Hct116 cells treated with R, while no such fluorescence images were observed from Hct116 cells used in control experiments (FIG. 11). These results confirmed the cell membrane permeability of this reagent and its ability to react with the intracellular Cysteine to initiate the demetallation reaction (Scheme 2) and regenerate L with fluorescence on response.

In vitro cytotoxicity of R on Hct116 cells (Colon cancer cell) was determined by conventional MTT (3-(4,5-Dimethylthiazol-2-yl)-2,5-diphenyltetrazolium bromide, a yellow tetrazole) assay. The assay revealed insignificant cytotoxicity towards Hct116 cells with $IC_{50}$ of 200 µM.

The present invention relates to a method for detecting cyanide ions among various anionic analytes under physiological conditions comprising solution with various anions in aq.-HEPES buffer pH 7.4 with reagent (R) and illuminating the sample and detecting the luminescence spectra.

Accordingly, the Luminescence spectra of the Ligand R in the absence and presence of 100 mole equivalents of various anionic analytes like $F^-$, $Cl^-$, $Br^-$, $I^-$, $CN^-$, $CH_3CO_2^-$, $H_2PO_4^-$, $P_2O_7^{4-}$, $HSO_4^-$, $NO_3^-$, $NO_2^-$, $N_3^-$, $ClO_4^-$, $PhCO_2^-$ and $IO_4^-$ in buffer media (pH 7.4) were recorded. Among all these anions, only $CN^-$ showed a turn-on emission response with maximum at 552 nm. Thus, along with Histidine and Cysteine, this reagent could also be used for detection of cyanide under the physiological condition.

The present invention provides a kit for carrying out the method for selective detection of cysteine and histidine in pure aqueous environment and in biological sample as well as for detecting endogenous Cysteine present in live Hct116 cells, without any interference from other amino acids comprising the following;
i. bis-Cu(II)-complex (R) of receptor ligand bis-dipicolyl amine derivative (L) of concentration 10 µm as fluorescence probe, excitable by spectrally separated wavelength of light, in pure aq.-HEPES buffer (pH 7.4) medium;
ii. 1 mMNEM solution;
iii. standard solution of histidine of concentration of 200 µM and 300 µM in pure aq.-HEPES buffer (pH 7.4) medium; and
iv. Instruction manual for performing the method.

The present invention provides a kit for use in carrying out the method for detection of cyanide ions among various anions under physiological conditions comprising;
i. bis-Cu(II)-complex (R) of receptor ligand bis-dipicolyl amine derivative (L) of concentration 20 µm as fluorescence probe, excitable by spectrally separated wavelength of light, in pure aq.-HEPES buffer (pH 7.4) medium;
ii. one or more standard solution in pure aq.-HEPES buffer (pH 7.4) medium; and
iii. Instruction manual for performing the method.

In another aspect, the present invention relates to use of novel bis-Cu(II)-complex (R) of receptor ligand bis-dipicolyl amine derivative (L) as fluorescence probe for selective detection of cysteine and histidine in pure aqueous environment and in human blood plasma as well as for detecting endogenous Cysteine present in live Hct116 cells without any interference from other amino acids.

The present invention relates to use of novel bis-Cu(II)-complex (R) of receptor ligand bis-dipicolyl amine derivative (L) as fluorescence probe for detection of cyanide ions among various anions under physiological conditions. The following examples, which include preferred embodiments, will serve to illustrate the practice of this invention, it being understood that the particulars shown are by way of example and for purpose of illustrative discussion of preferred embodiments of the invention.

EXAMPLES

The following examples are given by way of illustration and should not be construed to limit the scope of the present invention.

Example 1

Synthesis of L:

Compound 1 (210 mg, 0.625 mmol) and 2-Pyridinecarboxaldehyde (401 mg, 3.75 mmol) were dissolved in 7 ml of 1, 2 dichloromethane and refluxed it for 1 h. To this reaction mixture, Sodium triacetoxyborohydride (791 mg, 3.75 mmol) in 1,2 dichloromethane (10 mL) was added. The reaction mixture was allowed to stirring at room temperature for 48 h. Progress of the reaction was monitored by checking the TLC and stopped when no further change was observed. The reaction mixture was treated with saturated aqueous sodium bi carbonate solution and subsequent extraction using chloroform was performed. The organic layer was recovered, dried over anhydrous $Na_2SO_4$ and concentrated under reduced pressure. The crude product was subjected to neutral alumina gel chromatography using chloroform: methanol (99.5:0.5, v/v) as eluent. Major fraction was collected and dried under vacuum, which afforded a sticky oil solid. Yield: 270 mg, 61.78%.

Characterization Details:

ESI-Ms (m/z) calculated for $C_{40}H_{44}N_8O_2S$: 700, observed: 701 [M+H$^+$]. $^1H$ NMR [500 MHz, $CDCl_3$: δ (ppm)]: 8.45 (5H, d, J=3.5 Hz, ArH); 8.17 (1H, d, J=8.5 Hz, ArH); 8.01 (2H, d, J=7.00 Hz, ArH); 7.60 (4H, t, J=15 Hz, ArH); 7.46 (2H, t, J=8.5 Hz, ArH); 7.39 (4H, t, J=7.5 Hz, ArH); 7.11 (4H, t, J=6.00 Hz ArH); 3.66 (8H, s, $CH_2$); 3.38 (4H, t, J=7.0 Hz, $CH_2$); 2.85 (6H, s, $CH_3$); 2.52 (4H, t, J=7.0 Hz, $CH_2$). $^{13}C$ NMR (500 MHz, $CDCl_3$, δ (ppm173.6, 161.18, 145.80, 138, 137, 135.17, 129, 127.74, 124.24, 119, 50.24, 40.17, 32 and 31.60.

Example 2

Synthesis of R

The compound L (120 mg, 0.17 mmol) was dissolved in 7.5 mL methanol, to this Cu $(ClO_4)_2.6H_2O$ (126 mg, 0.342 mml) was added. Solution colour was changed immediately. The reaction mixture was stirred for 8 h and then transferred into a beaker and allowed to evaporation at room temperature to precipitate the desired compound. Light bluish white solid compound was isolated through filtration and was further carefully washed with cold Dichloromethane. Yield 120 mg, 42.25%. ESI-Ms (m/z) calculated for $C_{40}H_{44}Cu_2N_8.2H_2O$: 862, observed: 863 [M+H$^+$].

Example 3

Detection of Histidine in Human Blood Plasma

Pretreatment of the Healthy Human Blood Plasma for Estimation of $C_{Cys}$ & $C_{His}$:

Fresh and human blood samples (5 mL) with added Lithium anticoagulant were centrifuged in a vacutainer tube at 3000 rpm for 15 min. The supernatant solution (plasma), which contains proteins and amino acids, was collected. 2 ml of collected plasma was vigorously mixed with appropriate amount of $NaBH_4$ and incubated for 5 minutes at room temperature in order to hydrolyse the disulphide bond. Proteins present in the sample after reduction were precipitated by the addition of methanol, followed by centrifugation (18500 g) of the sample for 15 minutes. The supernatant liquid, which contained Cysteine and Histidine in blood plasma, was used for the spectroscopic studies.

Evaluation of $C_{Cys}$ and $C_{His}$ in Human Blood Plasma Sample

Methodology 1:

Calculation of the $C_{His}$ in Human Blood Plasma (HBP) sample that contains Cysteine and Histidine. To the 20 µM HBP sample 10 mM NEM was added. NEM is known to react irreversibly with Cysteine and yield a non-fluorescent compound (Scheme 2 shown below). The resultant solution was used for quantitative analysis of Histidine.

Scheme 2

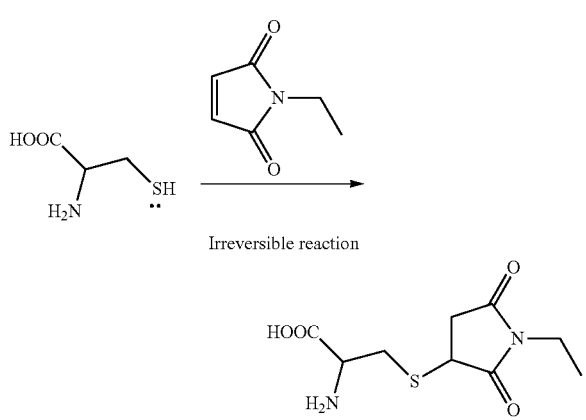

Irreversible reaction

Concentration of Histidine in HBP is low and thus to avoid any error in its detection, HBP samples (pre-treated with excess NEM) were spiked with two known concentration of His (200 µM and 300 µM, respectively). The fluorescence intensity of such HBP samples spiked with 200 and 300 µM of His were $I_{HBP+200}$ and $I_{HBP+300}$, respectively. Fluorescence intensities for pure aqueous HEPES buffer solution having pH of 7.4 was evaluated for [His] of 200 and 300 µM and these values were $I_{200}$ and $I_{300}$, respectively.

The difference between $I_{HBP+200}$ and $I_{200}$ led to the actual concentration of Histidine ($[His]_1$) in HBP sample. Similarly, the difference between $I_{HBP+300}$ and $I_{300}$ led to the actual concentration of His ($[His]_2$) in HBP sample. Arithmetic mean of $[His]_1$ and $[His]_2$ led to the value ((23±2.1) µM) for $C_{His}$ in HBP sample. The data reported for $C_{His}$ is an average of three independent evaluations for $[His]_1$ and $[His]_2$.

Emission intensity measurements for HBP samples treated with the reagent R directly gave the summation of concentration of $C_{Cys}$ and $C_{His}$ ($C_T = C_{Cys} + C_{His}$). Thus, $C_T - C_{His} = C_{Cys}$.

Methodology 2:

$C_{Cys}$ was also evaluated from the experiments with NEM that reacted specifically with Cys. Emission intensity for HPB samples treated with R was evaluated ($I_T$), which reflected the total concentration of Cysteine and Histidine present in HBP sample. The solution was then treated with NEM. NEM reacted with Cysteine present in HBP sample and the product was observed non emissive. The emission intensity ($I_{NEM}$) for the resulting solution was evaluated and the difference in intensities ($\Delta I = I_T - I_{NEM}$) was used for evaluation of [Cys] in HBP sample. Values evaluated for [Cys] in HBP sample, following this methodology, agreed well with the value that was evaluated by adopting the methodology 1.

Example 4

Cell Culture and Fluorescence Imaging: Confocal Laser Fluorescence Microscopic Images of Hct116 Cells.

Hct116 cells ($3 \times 10^5$) (procured from national repository of National Centre for Cell Science, Ganeshkind Road, Pune: 411007, Maharashtra, India) were seeded on coverslips placed in 6 well plates. After 24 hours cells were treated with R (10 µM) for 30 minutes or pre-treated with N-Ethyl Maleimide (NEM, a thiol specific blocking reagent (1 mM) for 30 minutes before adding R (10 µM) for 30 minutes. Cells were then washed thrice with Phosphate Buffer Saline (1×PBS) and fixed with 4% PFA for 20 minutes and washed again with 1×PBS. Permeabilization of the cells was done using 0.2% Triton X 100 for 5 minutes. Again three washes were given and then coverslips mounted using Fluor shield with DAPI (Sigma) mounting medium. Nail paints was used to seal the coverslips mounted on the glass slides. Images were acquired in Olympus Fluoview Microscope. Overlay of the merged images confirms the intracellular fluorescence. (FIG. 11)

Example 5

MTT Assay for Evolution of Cytotoxicity of the Reagent R Towards Hct116 Cells The in vitro cytotoxicity of R on Hct116 cells (Colon cancer cell) were determined by conventional MTT (3-(4,5-Dimethylthiazol-2-yl)-2,5-diphenyltetrazolium bromide, a yellow tetrazole) assay. Hct116 colon cancer cells ($7 \times 10^3$) were seeded in each well of a 96 well plate and cultured in a 37° C. incubator supplied with 5% CO2. Cells were maintained in DMEM medium, supplemented with 10% Fetal Bovine Serum and 100 Units of Penicillin Streptomycin antibiotics. After 24 hours the cells were treated with different concentrations of the R in triplicates for 12 hours. After treatment cells were added with 0.5 µg/ml of MTT reagent. The plate was then incubated for 4 hours at 37° C. and then later added to each well with 100 µl of Isopropyl Alcohol. The optical density was measured at 570 nm using Multiskan Go (Thermo Scientific) to find the concentration of the cell inhibition. $IC_{50}$ value was calculated to be 200 µM.

The formula used for the calculation of the MTT assay for evaluation of the cell viability is as follows:

Cell viability (%)=(means of Absorbance value of treated group/means of Absorbance value of untreated control)×100.

Advantages of the Present Invention

Novel bis-Cu (II)-complex (R) of ligand, bis-dipicolyl amine derivative (L) as 'turn on' fluorescent probe.

Quick process for selective detection and estimation of cysteine and histidine in pure aqueous environment and in a biological sample as well as for detecting endogenous Cysteine present in live Hct116 cells, without any interference from other amino acids. The reagent bis-Cu (II)-complex (R) can also be used for detecting cyanide ions among various anions under physiological conditions.

We claim:

1. A compound of formula R

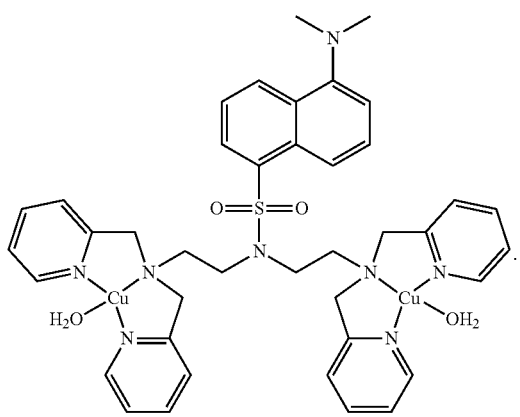

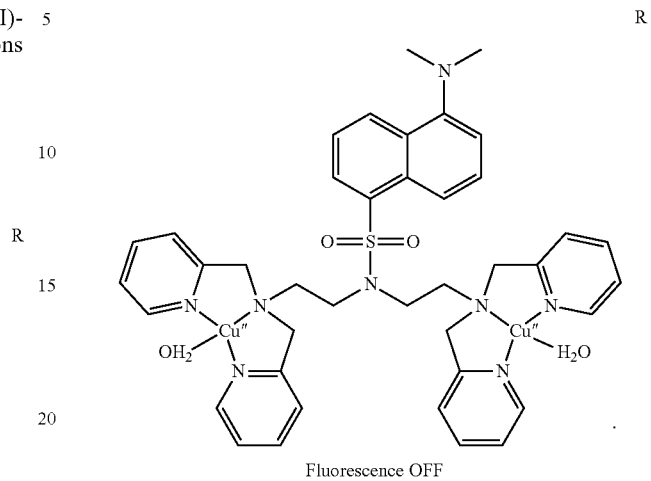

Fluorescence OFF

2. The compound as claimed in claim 1 is useful as a fluorescent probe for selective detection and estimation of amino acids.

3. The compound as claimed in claim 1, wherein the amino acids is selected from the group consisting of cysteine and histidine.

4. A process for synthesis of the compound as claimed in claim 1, comprising the process steps as:
   a) refluxing the mixture of solution of 5-amino-N,N-bis (2-aminoethyl) naphthalene-1-sulfonamide and 2-pyridine carboxaldehyde in a solvent at a temperature ranging between 60 to 80° C. for a period of time ranging between (1±0.5) hr followed by adding reducing agent in a solvent with stirring at a temperature ranging between room temperature for a period of time ranging between (20±4) hr. to get the reaction mixture;
   b) treating the reaction mixture obtained in step (a) with aqueous solution of base followed by extracting and drying to get crude product L;

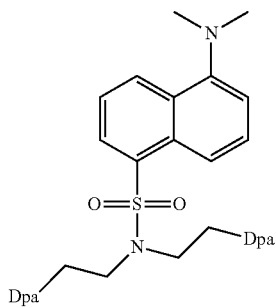

c) dissolving the crude product obtained in step (b) in a solvent with catalyst followed by stirring at a temperature ranging between 30 to 35° C. for a period of time ranging between (8±2) hr to get the compound R 5. The process as claimed in claim 4, wherein the solvent is selected from the group consisting of 1,2-dichloro methane, methanol and tetrahydrofuran.

6. The process as claimed in claim 4, wherein the aqueous solution of base is sodium bicarbonate.

7. The process as claimed in claim 4, wherein the reducing agent is selected from the group consisting of Sodium triacetoxyborohydride, Sodium bhorohydride and Sodium cyano bhorohydride.

8. A method for detection of total cysteine and histidine present in a biological sample using the compound as claimed in claim 1, comprising;
   i. providing a biological sample consisting an ensemble of all natural amino acids;
   ii. adding N-Ethylmaleimide (NEM) to the biological sample obtained in step (i);
   iii. spiking the biological sample pre-treated with NEM obtained in step (ii) with known amount of histidine;
   iv. adding bis-Cu(II) complex reagent (R) to the above solution of step (iii) ; providing control comprising pure aqueous HEPES buffer solution having pH of 7.4 of histidine;
   v. illuminating the sample solution and pure aqueous HEPES buffer solution having pH of 7.4 of histidine;
   vi. quantifying the amount of histidine and cysteine present in the sample solution.

9. The method as claimed in claim 8, wherein the concentration of HBP is in the range of 15-25 μM.

10. The method as claimed in claim 8, wherein the concentration of NEM is in the range 7.5-12mM.

11. The method according as claimed in claim 8, wherein the concentration of bis-CU(II) complex reagent (R) is in the range 15-25 μM.

12. A method for detecting intracellular cysteine using the compound as claimed in claim 1, comprising;
   i. incubating live Hct116 cells cells with bis-Cu(II) complex reagent (R) in aq.-HEPES buffer solution or optionally pre-treating the cells with NEM;
   ii. washing the solution obtained in step (i) with phosphate buffer solution (PBS);
   iii. providing a control comprising alive Hct116 cells without bis-Cu(II) complex reagent (R) in aq.-HEPES buffer solution;

iv. illuminating the above solution and determining the bright-red fluorescent image of reaction of R with intracellular Cysteine.

13. A method for detecting cyanide ions among various anionic analytes under physiological conditions comprising reacting the solution containing various anions in aq.-HEPES buffer pH 7.4 with bis-Cu(II)-complex (R) of claim 1 and illuminating the sample and detecting the luminescence spectra.

14. A kit for carrying out the method for selective detection of cysteine and histidine without any interference from other amino acids according to claim 8 comprising;
  i. bis-Cu(II)-complex (R) of receptor ligand bis-dipicolyl amine derivative (L) of concentration 10 μm as fluorescence probe, excitable by spectrally separated wavelength of light, in pure aq.-HEPES buffer (pH 7.4) medium;
  ii. 1 mM NEM solution;
  iii. standard solution of histidine of concentration of 200 μM and 300 μM in pure aq.-HEPES buffer (pH 7.4) medium; and
  iv. instruction manual for performing the method.

15. A kit for carrying out the method for detection of cyanide ions among various anions under physiological conditions according to claim 8 comprising;
  i. bis-Cu(II)-complex (R) of receptor ligand bis-dipicolyl amine derivative (L) of concentration 10 μm as fluorescence probe, excitable by spectrally separated wavelength of light, in pure aq.-HEPES buffer (pH 7.4) medium;
  ii. one or more standard solution in pure aq.-HEPES buffer (pH 7.4) medium; and
  iii. instruction manual for performing the method.

* * * * *